United States Patent [19]

Arai et al.

[11] 4,288,375
[45] Sep. 8, 1981

[54] NOVEL ORGANOSILANE COMPOUNDS

[75] Inventors: Masatoshi Arai; Koji Futatsumori, both of Annaka, Japan

[73] Assignee: Shin-Etsu Chemical Co., Ltd., Tokyo, Japan

[21] Appl. No.: 162,534

[22] Filed: Jun. 24, 1980

[30] Foreign Application Priority Data

Jun. 29, 1979 [JP] Japan .................................. 54-82451

[51] Int. Cl.³ .......................................... C07D 303/02
[52] U.S. Cl. .............................. 260/348.41; 556/479; 260/348.12
[58] Field of Search ..................................... 260/348.41

[56] References Cited

U.S. PATENT DOCUMENTS

| | | | |
|---|---|---|---|
| 2,637,738 | 5/1953 | Wagner | 556/479 |
| 2,823,218 | 2/1958 | Speier et al. | 556/479 |
| 3,687,606 | 8/1972 | Simmler et al. | 260/348.41 X |
| 3,702,783 | 11/1972 | Hartlein | 260/348.41 X |
| 4,069,368 | 1/1978 | Deyak et al. | 260/348.41 X |

Primary Examiner—Paul F. Shaver
Attorney, Agent, or Firm—Toren, McGeady & Stanger

[57] ABSTRACT

The invention provides a novel class of organosilane compounds having a glycidyloxy group and one or more of alkenyloxy groups bonded to the silicon atom as represented by the general formula

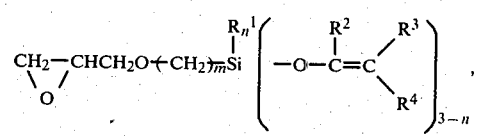

in which $R^1$ is a monovalent hydrocarbon group having from 1 to 8 carbon atoms, $R^2$, $R^3$ and $R^4$ are each a hydrogen atom or a monovalent hydrocarbon group having from 1 to 8 carbon atoms, m is an integer of 3, 4 or 5 and n is a number of zero, 1 or 2. The organosilane compound, e.g. 3-glycidyloxypropyl-containing alkenyloxysilanes can be readily prepared by the addition reaction of glycidyl allyl ether and a corresponding alkenyloxysilane having a hydrogen atom directly bonded to the silicon atom in the presence of a platinum catalyst. The organosilane compounds are useful as a coupling agent to increase adhesive bonding strength between inorganic and organic materials.

5 Claims, 2 Drawing Figures

NOVEL ORGANOSILANE COMPOUNDS

BACKGROUND OF THE INVENTION

The present invention relates to a novel organosilane compound having a glycidyloxy group and at least one alkenyloxy group bonded to the same silicon atom and a method for the preparation of the organosilane compound. The inventive organosilane compound is useful as a coupling agent to improve the adhesive bonding strength between organic and inorganic materials.

SUMMARY OF THE INVENTION

The invention provides a novel class of organosilane compounds hitherto unknown or not described in any prior art literatures represented by the general formula

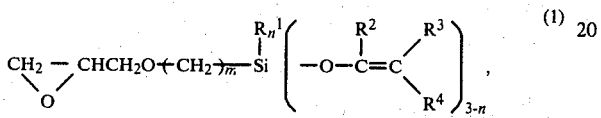

in which $R^1$ is a monovalent hydrocarbon group having from 1 to 8 carbon atoms, $R^2$, $R^3$ and $R^4$ are each a hydrogen atom or a monovalent hydrocarbon group having from 1 to 8 carbon atoms, m is an integer of 3, 4 or 5 and n is a number of zero, 1 or 2. In particular, the invention relates to an organosilane compound of the above given general formula (1) in which $R^1$ is a methyl, an ethyl or a phenyl group, $R^2$ is a methyl or an ethyl group, $R^3$ and $R^4$ are each a hydrogen atom or a methyl group, m is 3 or 5 and n is zero or 1.

The glycidyloxy- and alkenyloxy-containing organosilane compound of the general formula (1) can be readily synthesized by the addition reaction between a corresponding alkenyl glycidyl ether and a hydrogenalkenyloxysilane in the presence of a platinum catalyst.

DETAILED DESCRIPTION OF THE PREFERRED EMBODIMENTS

Figure 1:
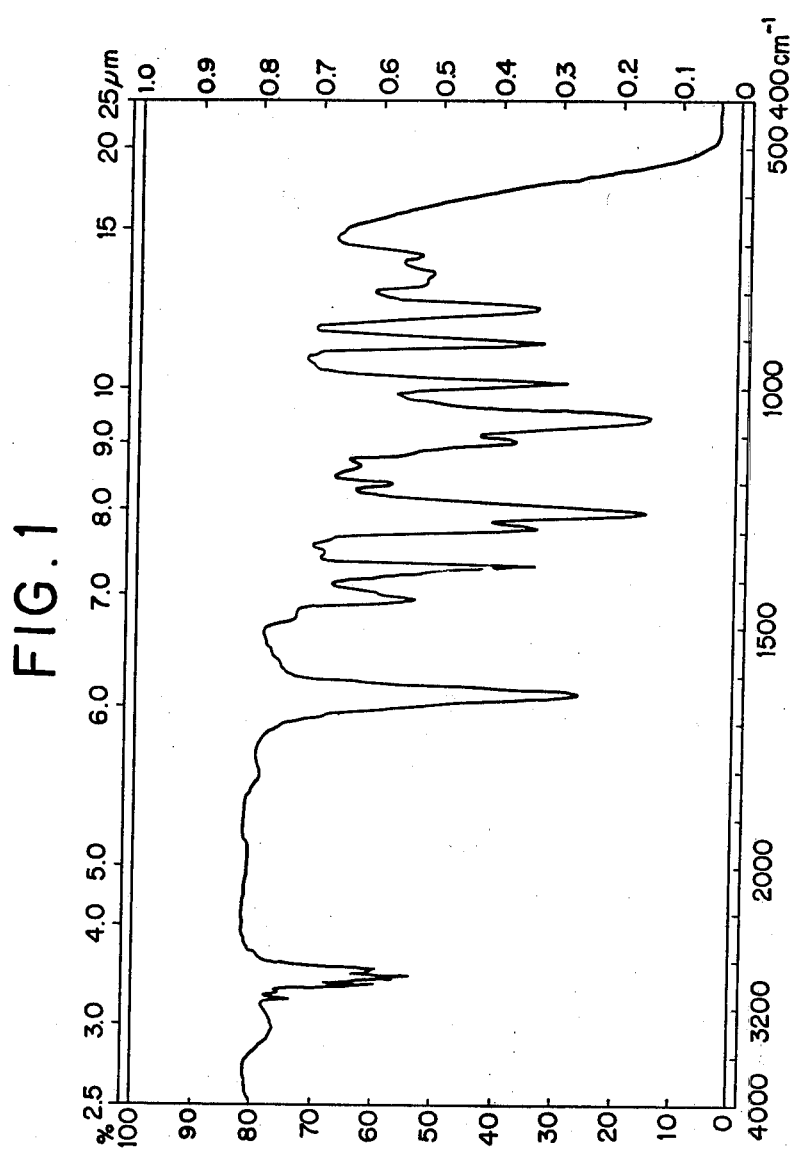
FIG. 1 and FIG. 2 are the infrared absorption spectra of the reaction products obtained in Example 1 and Example 2, respectively.

In the general formula (1) given above representing the inventive organosilane compounds, $R^1$ is a monovalent hydrocarbon group having from 1 to 8 carbon atoms exemplified by alkyl groups such as methyl, ethyl, propyl and butyl groups, alkenyl groups such as vinyl and allyl groups, aryl groups such as phenyl and tolyl groups and aralkyl groups such as benzyl group as well as those substituted hydrocarbon groups obtained by the substitution of halogen atoms, e.g. chlorine atoms, or cyano groups or other substituent groups for part or all of the hydrogen atoms in the above named monovalent hydrocarbon groups. In particular, the group $R^1$ is preferably a methyl group or a phenyl group although the group $R^1$ is not contained in the silane compound when the number n is equal to zero.

The symbols $R^2$, $R^3$ and $R^4$ in a molecule of the silane compound may be the same or different from each other and are each selected from the class consisting of a hydrogen atom and monovalent hydrocarbon groups having from 1 to 8 carbon atoms as exemplified by the same hydrocarbon groups as the examples of the group $R^1$. Preferably, the group $R^2$ is a methyl group or an ethyl group and the groups $R^3$ and $R^4$ are each a hydrogen atom or a methyl group.

The number represented by the symbol m is 3, 4 or 5 or, preferably, 3 or 5 so that the glycidyloxy-containing group bonded to the silicon atom of the inventive organosilane compound is a 3-glycidyloxypropyl or a 5-glycidyloxypentyl group. The number n is zero, 1 or 2 or, preferably, zero or 1.

Thus, several of the examples of the inventive organosilane compound of the general formula (1) in conformity with the above described preferred definitions of the individual symbols are shown by the following structural formulas (A) to (I), in which Me, Et and Ph denote a methyl, ethyl and phenyl group, respectively.

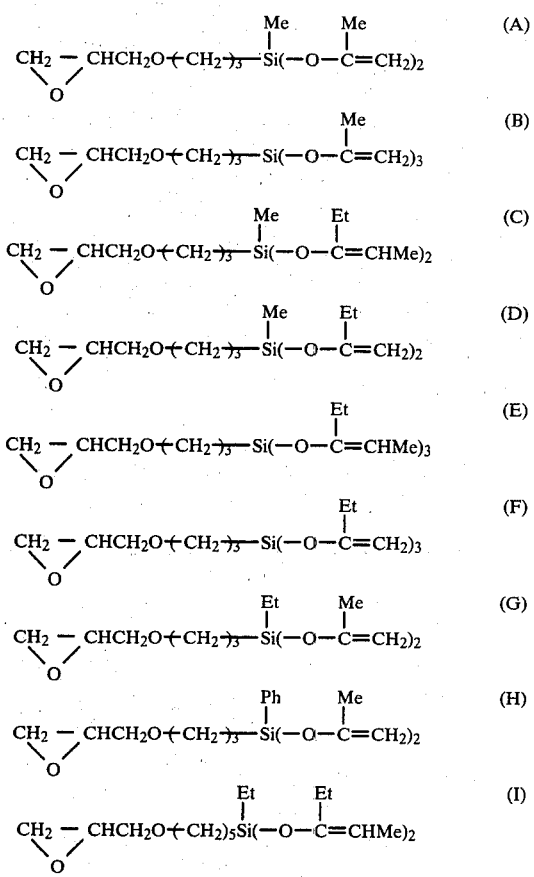

The organosilane compounds of the invention can be readily synthesized by the addition reaction between a corresponding glycidyl alkenyl ether and an alkenyloxysilane having a hydrogen atom directly bonded to the silicon atom. For example, the compounds of the above given structural formulas (A) and (B) are obtained by the addition reaction between glycidyloxy allyl ether and methyl di(isopropenyloxy)silane or tri(isopropenyloxy) silane, respectively. The addition reaction is accelerated by the catalytic action of a metal belonging to the eighth group of the Periodic Table, e.g. platinum, or a compound containing the same metallic element. By the way, the above mentioned alkenyloxysilane having a silicon-bonded hydrogen atom is obtained by the dehydrohalogenation reaction between a halogenohydrogensilane and an aldehyde compound or ketone compound which is subject to keto-enol tautomerism in the presence of an acceptor for the hydrogen halide.

The glycidyloxy- and alkenyloxy-containing silane compound of the invention is a carbon-functional silane of the deketonation type and exhibits excellent coupling effect for improving the adhesive bonding strength between inorganic and organic materials so that the inventive silane compounds are useful for improving the mechanical and electric properties of fiber-reinforced composite materials such as an epoxy resin-based FRP and the like.

Following are the examples to illustrate the synthetic preparation and the properties of the organosilane compounds of the invention.

EXAMPLE 1

Into a reaction vessel were introduced 46 g (0.40 mole) of allylglycidyl ether, 60 g of toluene and 0.05 g of an isopropyl alcohol solution of chloroplatinic acid containing 2.0% by weight of platinum. Into the reaction mixture kept at 60° C. were added 60.2 g (0.38 mole) of methyl di(isopropenyloxy)silane dropwise over a period of 30 minutes followed by heating at 80° C. for additional two hours to effect the addition reaction.

The reaction mixture was subjected to distillation under reduced pressure to give 85 g of a fraction boiling at 119° C. under a pressure of 5 mmHg. This liquid product was identified to be 3-glycidyloxypropyl methyl di(isopropenyloxy)silane expressed by the structural formula (A) given above from the analytical results given below together with the value of the refractive index. The above given yield of the compound corresponded to 82% of the theoretical value based on the amount of the starting silane compound.

| | Elementary analysis: | |
| | Calculated, %, as $C_{13}H_{24}O_4Si$ | Found, % |
|---|---|---|
| C | 57.32 | 57.30 |
| H | 8.88 | 8.92 |
| Si | 10.31 | 10.28 |

Molecular weight by mass spectrometry: 272 (calculated value as $C_{13}H_{24}O_4Si$ 272).
Refractive index $n_D^{25}$:1.4520.
Infrared absorption spectral analysis: see FIG. 1.

EXAMPLE 2

The reaction was carried out in the same manner as in Example 1 except that 60.2 g of methyl di(isopropenyloxy)silane used in Example 1 were replaced with 65.4 g (0.38 mole) of tri(isopropenyloxy)silane. Distillation of the reaction mixture after the reaction under reduced pressure gave 72.9 g of a fraction boiling at 140° to 142° C. under a pressure of 5 mmHg. This liquid product was identified to be 3-glycidyloxypropyl tri(isopropenyloxy)silane expressed by the structural formula (B) given above from the results of analyses given below together with the value of the refractive index.

The above given yield of the product was about 61% of the theoretical value based on the amount of the starting silane compound.

| | Elementary analysis: | |
| | Calculated, %, as $C_{15}H_{26}O_5Si$ | Found, % |
|---|---|---|
| C | 57.29 | 57.34 |
| H | 8.33 | 8.29 |
| Si | 8.93 | 8.90 |

Figure 2:
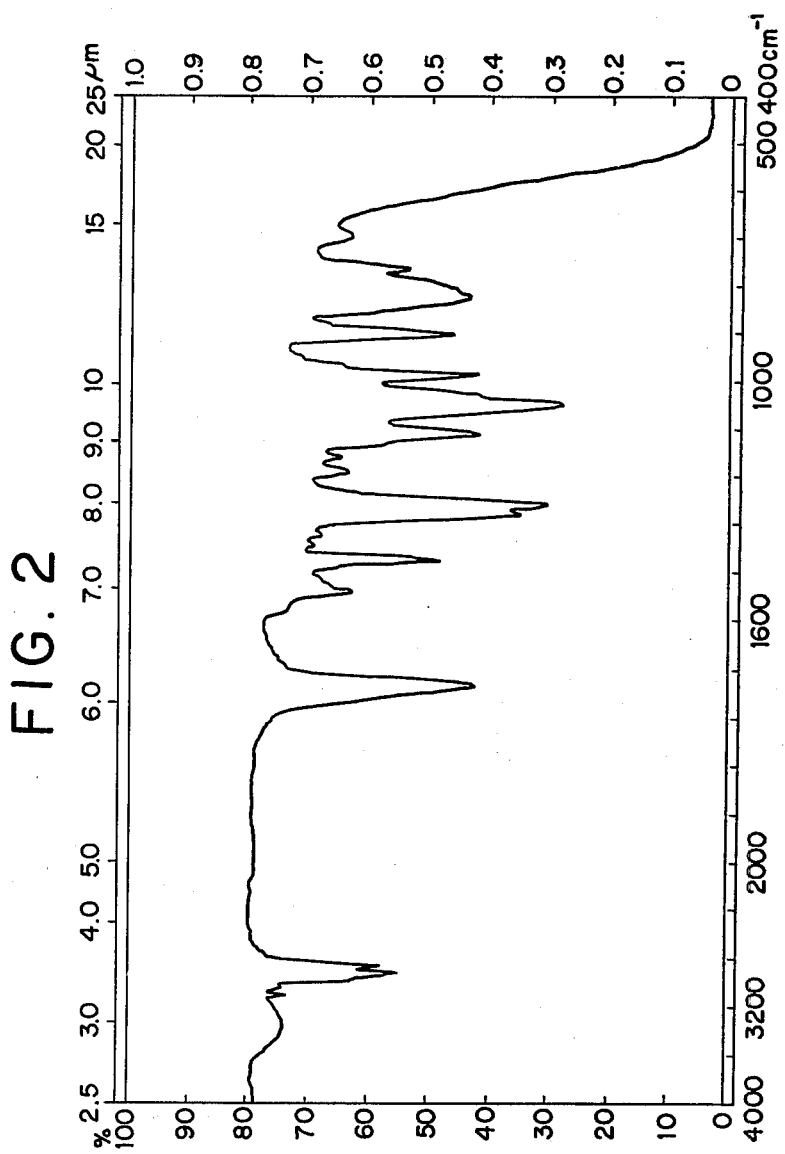

Molecular weight by mass spectrometry: 314 (calculated value as $C_{15}H_{26}O_5Si$ 314).
Refractive index $n_D^{25}$:1.4535.
Infrared absorption spectral anaylsis: see FIG. 2.

EXAMPLE 3

The experimental procedure was almost identical with that in Example 1 except that the methyl di(isopropenyloxy)silane was replaced with equimolar amount of an alkenyloxysilane expressed by the structural formula

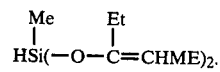

The reaction product obtained by distillation under reduced pressure had a boiling point of 139° C. under 1 mmHg and a refractive index $n_D^{25}$ of 1.4594 and was identified from the results of analyses to be the organosilane compound expressed by the structural formula (C) given above. The yield of the product was about 65% of the theoretical value based on the starting silane compound.

EXAMPLE 4

The experimental procedure was almost identical with that in Example 1 except that the methyl di(isopropenyloxy)silane was replaced with equimolar amount of an alkenyloxysilane expressed by the structural formula

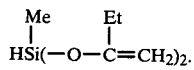

The reaction product obtained by distillation under reduced pressure had a boiling point of 132° C. under 2 mmHg and a refractive index $n_D^{25}$ of 1.4540 and was identified from the results of analyses to be the organosilane compound expressed by the structural formula (D) given above. The yield of the product was about 67% of the theoretical value based on the starting silane compound.

What is claimed is:

1. An organosilane compound represented by the general formula

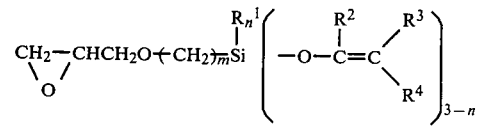

in which
$R^1$ is selected from the class consisting of methyl, ethyl and phenyl groups,
$R^2$ is a methyl or an ethyl group, $R^3$ and $R^4$ are each a hydrogen atom or a methyl group, m is 3 or 5, and n is zero or 1.

2. The organosilane compound as claimed in claim 1 which is 3-glycidyloxypropyl methyl di(isopropenyloxy)silane.

3. The organosilane compound as claimed in claim 1 which is 3-glycidyloxypropyl tri(isopropenyloxy)silane.

4. The organosilane compound as claimed in claim 1 which is a compound expressed by the structural formula

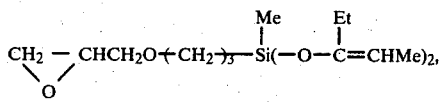

in which Me and Et denote methyl and ethyl groups, respectively.

5. The organosilane compound as claimed in claim 1 which is a compound expressed by the structural formula

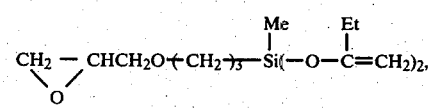

in which Me and Et denote methyl and ethyl groups, respectively.

* * * * *